US006953849B2

(12) United States Patent
Vali et al.

(10) Patent No.: US 6,953,849 B2
(45) Date of Patent: Oct. 11, 2005

(54) PROCESS FOR THE ISOLATION OF GLYCOLIPIDS

(75) Inventors: Shaik Ramjan Vali, Hyderabad (IN); Pradosh Prasad Chakrabarti, Hyderabad (IN); Narayana Balagopala Kaimal Thengumpillil, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 441 days.

(21) Appl. No.: 09/820,200

(22) Filed: Mar. 28, 2001

(65) Prior Publication Data

US 2002/0143173 A1 Oct. 3, 2002

(51) Int. Cl.$^7$ .......................... C07H 11/04; C07H 13/00
(52) U.S. Cl. ............................ 536/117; 554/9; 554/117
(58) Field of Search ..................... 554/175, 9; 536/117

(56) References Cited

U.S. PATENT DOCUMENTS 4,533,501 A * 8/1985 Sen Gupta .................. 260/428

* cited by examiner

*Primary Examiner*—Raymond Henley, III
*Assistant Examiner*—C. Delacroix-Muirheid
(74) *Attorney, Agent, or Firm*—Ladas and Parry LLP

(57) ABSTRACT

The present invention relates to a process for the isolation of a glycolipid enriched fraction from rice bran oil by subjecting crude rice bran oil to at least two steps of dewaxing/degumming, treating sludge obtained as a byproduct of the second said dewaxing/degumming to hexane extraction, and separating the glycolipid fraction. The glyolipid fraction so obtained can be further purified.

8 Claims, No Drawings

PROCESS FOR THE ISOLATION OF GLYCOLIPIDS

FIELD OF THE INVENTION

The present invention relates to a progress for the isolation of glycolipids from crude rice bran oil. The present invention particularly relates to a progress for isolating and recovering a high-value glycolipid product from the rice bran oil.

BACKGROUND OF THE INVENTION

Glycolipids are glycosyl derivatives of lipids such as acylglycerols, ceramids and prenols. They are components of cell membranes found in species ranging from bacteria to man. Because of the diversified structures, glycolipids perform a variety of functions in living organisms (Curatolo, W. *Biochim. Biophys. Acta,* 906, 1987, 111–136). In recent years, a wide number of new glycolipids have been synthesized or isolated from natural sources. The role of glycolipids in various organisms, organs, tissues and membranes is currently attracting a lot of attention (Curatolo, W. *Biochim. Biophys Acta,* 906, 1987, 137–160).

The physiological functions of glycolipids are yet to be understood completely. It appears that glycolipids serve four general functions in cell membranes; stablilization, shape determination, recognition and ion-binding (Curatolo, W: *Bichem. Biophys. Acta,* 906, 1987, 137–160). Certain glycolipids carry out similar functions whether they are observed in bacteria, plants or animals. Some of these are:

1. Impart structural integrity and decreased permeability to myelin membranes in mammalian brains (Oldfield, E. and Chapman, D, *FEBS Lett.,* 21, 1972, 393–306, Ladbrooke, B. D., et al, *Biochim. Biophys. Acta,* 164, 1968, 101–109).
2. Provide stabilization to the brush border membranes intestinal epithelium (Hauser, H., et al, *Biochim, Biophys, Acta,* 610, 1980, 567–577; Br4cimer, M. E., et al, J. Biol, Cihem, 257, 1982, 557–568; Brasitus, T. A., and Schachter, D. *Biochemistry,* 19, 1980, 2763–2769); also membranes of the tubules of kidney (Karisson, K. A., et al, *Biochim. Biophys. Acta,* 316, 1973, 317–335; Tomono, Y., et al, *Biochim. Biophys. Acta.* 796, 1984, 1999–204) and human colon (Corfield, A. P. et al, *Biochem, Soc., Trans,* 19(2), 1991, 220).
3. Act as a permeability barrier of stratum corneum, the outer most layer of the skin (Gray, et al, *Br. J. Dermatol,* 106, 1982, 59–63); and
4. Function are receptors for virus and bacteria (Haywood, A. M. *J. Mol. Biol,* 87, 1974, 625–628), carbohydrate binding proteins, plant and animal lectins (Surolin, A., et. al, *Nature,* 257, 1975, 802–804; Rando, R. R. and Bangerter, F. W., *J. Supramol. Struct.* 11, 1979, 295–309; Wassef, N. M. et al, *Biochem. Biophys. Res. Commun.* 130, 1985, 76–83), bacterial toxins including cholera toxins (Van Heyningen, S. *Science,* 183, 1974, 656 657), tetanus toxins (Van Coli entereotonins (Moss, J., et. al, *J. Biol, Chem,* 256, 1981, 12861–12865) etc. and hormones (Mullin, B. R. et al, *Proc. Natl. Acad. Sci.* USA, 73, 1976, 842–846; Becker, S. K. et al., *Proc. Natl. Acad. Sci.* USA, 78, 1981 4848–4852, Fishman, P. H., et al. *J. Biol. Chem.* 250, 1984, 7983–7989).

Glycolipids play an important role in human health. It has been reported that qualitative and quantitative changes in the glycolipids of cells occur during differentiation and oncogensis (Hakomori, S. *Biochim. Biophysm Acta,* 417, 1975, 55 89; Feizi, T., *Nature,* 314, 1985, 53–57). Extensive analysis of the glycolipids of tumorous tissues showed both quantitive and quatitative differences with normal tissues (Hamomori, S. and Murakami, W. T., *Proc. Natl. Acad. Sci.,* USA, 59, 1968, 254–261). Antibodies were used to characterise a variety of tumor antigens which were carried on gangliosides (Tai, T., et al., *Biochim. Biophys, Acta,* 835, 1985, 577–583) and neutral glycosphingolipids (Willison, K. R., et al. *J. Biol. Chem,* 1983, 4091–4097). These extensive studies of glycolipid antigens on cell surfaces have provide wealth of information related to glycolipid synthesis and the nature of the cell surface in differentiation and oncogenesis.

Glycolipids have been implicated in a variety of immunological phenomena. The possible involvement of gangliosides in the action of interferon was reported long back (Bensancon, F. and Ankel, I I *Nature,* 252, 1974, 478–480). Interleukin-2 was shown to have affinity towards gangliosides (Parker, J., et al, *FEBS Lett.,* 170, 1984, 391–395). However, the area still remains wide open as another group of scientist showed that although gangliosides binds interleukin-2 in vitro, it is unlikely that these glycolipids act as physiologically relevant interleukin-2 receptors (Robb, R. J. *Immumol,* 136, 1986, 971–976). Involvement of glycolipids in lymphocyte stimulation has been suggested by a series of studies (Spiegel, S., et al., *Proc. Natl. Acad. Sci.,* 76, 1979, 5277–5281; Spiegel, S and Wilchesk, M. *J. Immunol,* 127, 1981, 572–575; Spiegel, S. and Wilcheck, M., *Mol. Cell. Biochem.* 55, 1983, 183–190). It was also indicated that the ganglisides may be involved in immuno regulations (Miller, H. C. and Essenman, W. J. *J. Immunol.* 115, 1975, 839–843); Chaney, W. G. et. al., *Cell Immunol.* 86, 1984, 165–170). Inhibitation of concanavalin 4-induced mitogentic response in mouse thymocytes by the gangliosides was demonstrated (Langle, E. E. et al., *Cancer Research,* 39, 1979, 817–822). In another communication, possible immunosuppressive effect of gangliosides shed from tumor cells was indicated (Ladish, S, et. al., *Cancer Research,* 43, 1983, 3808–3813).

The involvement of gangliosides in the growth of neutrons is well established. Extensive proliferation of neutires of felines with gangliosidosis was observed (Purpura, D. P. and Baker, H. *J Brain Res.,* 143, 1978, 13–26). These effects could be elicited by a variety of purified gangloslides (Byrene, M. C., et al, *J. Neurochem.,* 41, 1983, 1214–1222). The promising in vitro results was followed by attempts to cure neuropathies with ganglioside injections (Gorio, A. et al, in *Ganglioside Structure, Function and Biomedical Potential,* Ed. by Ledeen, R, Yu, R, Raport, M and Suzuki, K. Plenum Press, New York, 1984, 549–561). Initial clinical trials on humans indicated that gangliosides injections may improve symptoms of diabetic neuropathy (Narden, A., et al., in *Ganglioside Structure, Functions and Biomedical Potential,* ed. By Ledeen, R, Yu, R., Rapoort, M and Suzuki, K, Plenum Press, New York, 1984, 593–600).

The mechanism of the actions of various glycolipids in regulating physiological function are yet to be understood and in recent years, extensive studies are being carried out throughout the world on the biological activities of glycolipids isolated from various natural resources as well as of synthetic glycolipids. The use of glycolipids in pharmaceurical and cosmetic preparations is increasing at a brisk pace.

In a recent communication, possible use glycodlipids from sivers sagebrush (wormwood) as organoleptic and biologically active additive in food industries were evaluated (Gubanenko, G. A., et al, *Pischch. Prom.* St. 6, 1998, 26–27). Glyocolipids are implicated for many physiological functions and based on these findings, newer drugs were being formulated. Cell uptake and transfection efficiency of DNA/glycolipid complexes were implicated as potential HIV-1 fusion cofactor by a group of scientists (Djilalj, H., et al, *Biochim, Biophys. Res. Commun.* 246(1), 1998, 117–122). U.S. Pat. No. 5,871,714 discloses the use of glycolipid-based compositions for controlling of colonization of bacterial plaque in the oral cavity (Bundy, J. A. 1999). PCT Int. Appl. WO 99,00136 discloses another formulation comprising of glycolipids for use in treatment or prohylaxis or acidic gut syndrome resulting from accumulation of acids and production of endotoxins in the gastrointestinal tract (Rowe, J. B., 1999). The role of glycolipids on age related changes of the brain and also in Alzheimer's disease was reviewed recently (Endo, T. *Tampakskitu Kakusan Koso,* 43 (16), 1998, 2582–2588). In another communication, the role of glycolipids in type 1 diabetes and lupus, in intracellular bacterial infections and in tumor rejections were reviewed (Park, S. II. et al, *Semin. Immunol.,* 10(5), 1998, 391–398). Structural features and biological activities of some natural and synthetic glycolipid antigens which induce a CD-1 restricted T-cell response are discussed in PCT Int, Appl. WO 99,12562 (Porcelli, S. A. and Moody, D. B., 1999). These glycolopids can be used for treatment of individuals infected with *Mycobacterium leparae.* Glycolipids were found to have an important role in lens fiber developed in human eye (Ogiso, M, *Acta, Biochim. Pol.,* 45 (20, 1998, 501–507).

Sophorolipids are very important glycolipids which can be isolated from various sources (Marchal, R., et al., U.S. Pat. No. 5,900,366, 1999: Daniel; H. S. et al, *Biotechnol.,* 51 (1), 1999, 40–45). In one investigation, sophorolipid was produced from deproteinized whey and rapessed oil (Daniel, H. S., et al, *Biotechnol, Lett,* 29(12), 1998, 1153–1156). Bioactivity of the extracellular glycolipids like sophorolipids and sophorolipid-derivatives were investigated (Sholtz., C., et al., *Polym, Prepr.* 39 (2), 1998, 168–169). These glycolipids were found to exhibit cell growth inhibition properties for Jurkat (Leukemia) and Tu-138 (head and neck cancer) cells. Glycosylphosphotidyl inositols represent predominant class of glycolipids synthesized by the asexual intra-erythrocytic stages of *Plasmodium falciparum.* These glycolipids have an effect on material toxins and in release of cytokines like tumor necrosis factor- and interleukin-10 (Schmidt, A., et al, *Exp. Parasitol.,* 88(2), 1998, 95–102).

Japanese scientists have isolated a new glycolipid from *Gigartina tenella* (Ohra K, et al., *Jpn. Kokai Tokkyo Koho,* JP 11, 106,395, 1999). This glycolipid from red seawood was found to be highly active as DNA-synthetase B-inhibitor, HIV inhibitor and as immunosuppressant. This was also found to act as anti-cancer agents along with some other immunosuppressive effects (Yoshida, M., et al., *Jpn Kokai Tokkyo Koho* JP, 10, 152,498, 1998). Clusters of glycolipids and glycophosphotidyl inositol-anchor proteins in lymphoid cells were investigated for their cellular responses to raft patch formation in the Jurkal (Leukemia) T-cell lines and, in particular, changes in the actin cytoskeleton (Harder, T. and Simons, K., *Eur., J. Immunol,* 29 (2), 1999, 556–562). Growth factor-induced release of a glycosyl-phosphatidyl inositol (GPI)-linked protein from HEP-2 human carcinoma cell lines was studied by a group of English scientists (Roberts, J. M., et, al., *FEBBS Lett.,* 267 (2), 267 (2), 1996, 213–216). The suitability of glycolipids in gene therapy was also tested by a group of scientists (Havermann, K., et. al, EP 893,493, 1999).

Glycolipids are excellent surface-active agents. In fact, a majority of naturally occurring surfactants (bio-surfactants) are glycolipids. However, bio-sufactants are fermentation products and their commercial productions, at present, are not economically feasible. In context, their isolation from cheap natural products such as rice bran oil assumes importance. A few of the glycolipids isolated from other natural resources have been tested for then surface active properties. Because of the complete biodegradability, these are being evaluated for special uses. Glycolipids were used as synergists in a detergent formulation made for manual dishwashing (Udo, H., et, al., Ger. Offen. DE 19,648,439, 1998). Glyolipid based biosurfactant complexes, produced by micro-organisms of *Rhodococcus* species was used for oil desorption from minerals and organic materials (Ivashina, I. B., et, al., *J. Microbiol. Biotechnol,* 14(5), 1998, 711–717). Another glycolipid type of biosurfactant was obtained from a strain of *Pseudomonus Aerugmosa* isolated from soil (Cho, J. H., et al., *J. Mirobiol. Biotechnol,* 8(6), 1998, 645–649). Critical microllar concentration of this surfactant was found to be very low—as low as 50 ppm and the minimum surface tension was obtained was 30.1 mN/m. It showed very good emulsifying property, better than a well known emulsifier like emulsan. Foaming power and emulsifying properties of some other glycolipid-based biosurfactants isolated from pumpkin were evaluated (Nakac, T., et al., *Food Sci, Technol. Int.* 4(3), 1998, 235–240). These surfactants also showed good foaming power and emulsifying properties comparable to any commercial surfactant. A group of German scientists have described a method for the microbial production of surface active glycolipids from vegetable oil and carbohydrates (Lang, S., et al, *Food Sci, Technol. Int.,* 4(3), 1998, 235–240). These surfactants also showed good foaming power and emulsifying properties comparable to any commercial surfactant. A group of German scientists have described a method for the microbial production of surface active glycolipids from vegetable oils and carbohydrates (Lang, S., et al., *Schrifter. Nachwachsende Rohst,* 10, 1998, 154–163). The glycolipid formed by this method reduced the surface tension of water from 72 to 32 mN/m. Rhamnolipids and sophrolipids are two glycolipids that show considerably high degree of surface activities. Recently a facile procedure for remediation of oily with rhamnolipid biosurfactant was reported(Nakata, K. and Ishiggami, Y., *J. Environ, Sci, Health—Part A: Toxic/Hazard. Subst. Environ. Eng. A* 34(5), 1999, 1129–1142). A simple remediation process for mousse oil wastes was carried out using rhamnolipid as bioemulsifier. The feasibility of using biosurfactants to remove heavy metals from an oil contaminated soil was evaluated by hatch washes with surfacing, a rhamnolipid and a sophorolipid and the results obtained were quite encouraging (Mulligan, C. N., et. al., *Environ. Prog.,* 18(1), 1999, 50–54).

With such wide ranging nature, functions and biological activities, it is surprising that these compounds are not exploited commercially and great extent. Possible reasons for this could be the lack of availability of natural sources rich in these glycolipids or commercially viable processes for their isolation. Rice bran oil appears to offer significant possibilities on these count glycolipids content is quite high. These glycolipids contain a number of compounds of wide structure complexities including a novel phosphorus containing glycolipid identified by the present authors (unpublished) and these can be isolated by simple, commercially processes as detailed in the present invention.

India is the second largest producer of rice (after China). About 2.8 million tons of rice bran is processed in India every year yielding about 500,000 tons of rice bran oil. Crude rice bran oil of Indian origin contains 2–3.5% of waxes, 1–2% of gums (phosphatides) and 2.5–3.5% of glycolipids (Kyong-Soohm, et al, *Han'guk Sikp'um Younygang Kwahack Hocchi,* 25(5), 1996, 735–740). To get a better quality of edible oil as well as for the smooth operation of the later processing steps, the removal of both waxes and gums are necessary. Dewaxing is generally done at the final stages of refining by the process of winterization whereas degumming is done before alkali neutralization.

Crude rice bran oil shows an unusual behaviour as compared to the other vegetable oils. It can hold its own volume of hot water without the water separating out from the oil This property was taken advantages of in developing a process for simultaneous degumming and dewaxing of the oil (Kaimal, T. N. B., et al., Indian Patent No. 183639, 2000). This particular property was also not observed in high phospholipid containing oil like soybean oil and wax containing oil like sunflower oil and probably arises from the high content of glycolipids in the rice bran oil. Moreover, in contrast to other vegetable oils, rice bran oil contains a number of special types of glycolipids. A series of steryl glycosides (Fujino. Y. et al., *Biochim. Biophys. Acta,* 574, 1979, 94), ceramides and ceramide monohexocides were reported in the bran (Fujino, Y. et al, *J. Food Sci.,* 39, 1974, 471; Fujino, Y. et al, *Chem, Phys, of Lipids,* 17, 1976, 275) and different glyceroglycolipids (Sasyty, P. S. et al., *Biochemistry,* 3, 1964, 1271; Miyano, M., et al., *J. Am. Oil Chem. Soc.,* 57, 1962, 84) have also been reported in rice bran. The water absorbing capacity of rice bran oil may be attributed to the presence of these special types of glycolipids. The sludge generated in degumming/dewaxing of rice bran oil was found to contain the whole amount of water used in the degumming/dewaxing operation in a smooth emulsified form and this also may be attributed to the presence of mixture of glycolipids like ceramides, sphingolipids, steryl glycosides etc. The emulsion obtained was very strong and was strong and was stable for a long time. The analysis of that sludge, indeed shoed the presence of higher amount of glycolipids. It is well documented that not only in the bran but also in the rice bran oil the glycolipid content is very high compared to the other oils. It was also reported that the glycolipids fraction of rice bran oil contains a mixture of different types of glycosides, glyceroglycolipids, sphingolipids and ceramides group of compound (Nasirullah and Nagaraia, K. V., *J. Oil Tech, Asso, India,* 19, 1987, 2; Kyong-Soohn, et al, *Han'guk Sikp'um Yonygang Kwahak Hoechi,* 25(5), 1996, 735; Fujino, Y. and Ohnishi, M., *Chem. And Phys. Of Lipids,* 17, 1976, 275).

These glycolipids, if isolated, can be used in various foods, pharmaceuticals and nutraceutical formulations. These glycolipids may find their uses in cosmetics industries as well. It is widely accepted that the rice bran oil has many nutritional and health benefits. This is attributed mainly to γ-oryzanol, a constituent of rice bran oil. However, the nutritional aspects of the novel glycolipids present in rice bran oil are yet to be investigated and these glycolipids may also contribute to the extraordinary health benefits shown by rice bran oil.

A few attempts have also been to utilize the various glycolipids present in rice bran and rice bran oil. In recent patent (Jpn. Kokai Tokkyo Koho, JP 11,113,530, 1999), it was claimed that the ceramides extracted from rice bran can be utilized to prepare a formulation which shows skin-moisturizing, rough skin-preventing and anti-wrinkle effects. In another patent (Ger. Offen. DE 4,130,915, 1992), sphingolipids were used as an important ingredient in a scalp and skin-moisturizer formulation. It was also observed that the sphingolipids could be combined with conventional ingredients to provide a shampoo that inhibits dandruff formation by more than 50%. The added advantages of these molecules are they show very high activity even at a very low concentration. Rice bran extracts reportedly were used in the preparation of hair growth stimulants (South African Patent ZA 92,00186, 1992). Significant amount of ceramides and sphingolipids are present in rice bran (Fujino, Y. and Ohnishi, M *Chem. Phys. of Lipids,* 17, 1976, 275). These sphingolipids, ceramides and their derivatives may also be used for the same purpose. A bath preparation that prevents itching and eczema of the skin was patented (Jpn. Kokai Tokkyo Koho, JP 09, 118,614, 1997) which has ceramides as an important ingredient. Apart from the examples cited above, there exist a number of cosmetic formulations, which are based on rice bran oil extracts or rice bran oil itself (Jpn, Kokai Tokkyo Koho, JP 09, 12, 443, 1997; Jpn. Kokai Tokkyo Koho, JP 06,345,635, 1994; Jpn. Kokai Tokkyo Koho, JP 02,264,706, 1990; Jpn. Kokai Tokkyo Koho, JP 11,05,730, 1999). In all these processes, the glycolipids used in the formulations were isolated from rice bran or the other sources by using the conventional methods.

Glycolipids are conveniently isolated in the laboratory by (I) extraction of the total lipids with $CHCl_3/CII_3OII$ (2:1 v/v) and water saturated butanol and (ii) silicic acid column chromatography employing sequential elution with $CHCl_3$, acetone and $CH_3OH$ (Fujino, Y. and Ohnishi, M. *Chem. Phys. of Lipids,* 17, 1976, 275) to yield three fractions containing neutral lipids, glycolipids and phospholipids respectively (Rouser, G. et al, Lipids, 2, 1967, 37). This method has also been followed to isolate glycolipids from rice bran oil (Fugino, Y. et al, *Biochim, Biophys. Acta,* 574, 1979, 94). This laboratory method, however, is not easily adapted by the industry because the method requires large amount of solvents and it is time-consuming as well. In view of these difficulties, no serious efforts were made to isolate the glycolipids present in the rice bran oil for commercial explorations. Japanese scientists, in an alternative way of isolation, used latrobeads column to recover glycolipids from soy protein isolates (Homma, S. and Murata, M *Darzu Tanpakushitur Kenkyakai Kaishi,* 14, 1993, 104). In a more recent communication, a method to isolate a specific glycolipid from boar spermatozoa using ion-exchange chromatography in combination with partition chromatography was described (Iga, D. P., et. al., *Bio,* 45, 1996, 9). The major drawbacks of these processes are that these are expensive and time consuming.

OBJECTS OF THE INVENTION

The main object of the invention is to provide an easy and convenient method to isolate glycolipids from the sludge generated in the simultaneous degumming/dewaxing process of rice bran oil.

Another object of the invention is to provide a process for the isolation and recovery of glycolipids, a mixture of glyceroglycolipids, sphingolipids, ceramides etc. (either in fraction or as a whole) from crude rice bran oil.

Still another object of the invention is to isolate and recover the glycolipids from the waste sludge produced during the simultaneous degumming/dewaxing of rice bran oil as described in an earlier patent (Kaimal, et al, Indian Patent No. 183, 639, 2000).

SUMMARY OF THE INVENTION

Accordingly the present invention provides a process for the isolation of a glycolipid enriched fraction from rice bran oil, said process comprising subjecting crude rice bran oil to at least two steps of dewaxing/degumming treating sludge obtained as a byproduct of the second said dewaxing/degumming to hexane extraction, and separating the glycolipid fraction.

In another embodiment of the invention, the glycolipid fraction is purified to obtain substantially pure glycolipids.

In a further embodiment of the invention, the purification of the glycolipid fraction is done by column chromatography.

In another embodiment of the invention, the glycolipid fraction is separated by centrifugation and lyophilisation.

The invention also relates to a process for the isolation of a glycolipid fraction from rice bran oil, said process comprising degumming/dewaxing the crude rice bran oil by adding boiling water thereto with stirring to form an emulsion, separating the emulsion thus obtained into a supernatant fraction and sludge, subjecting the supernatant fraction to further degumming/dewaxing by adding water at elevated temperature with stirring, separating the resultant emulsion into a supernatant fraction containing substantially pure oil and a sludge, extracting at least once the sludge so obtained with hexane followed by separating the said glycolipid fraction.

In another embodiment of the invention, the glycolipid fraction is purified to obtain substantially pure glycolipids.

In a further embodiment of the invention, the purification of the glycolipid fraction is done by column chromatography.

In another embodiment of the invention, the glycolipid fraction is separated by centrifugation and lyophilisation.

DETAILED DESCRIPTION OF THE INVENTION

The most important advantage of the process is that since the concentration of glycolipids in the sludge is much higher than that in oil, the isolation becomes easier. On the other hand, the present invention utilizes the sludge (which is of no value or having a meager price) to recover a high value product like glycolipids.

Generally, in industry degumming is carried out by heating the oil to 60–70° C. and by adding water (the amount of water being close to the phosphatide content) under stirring condition. The gums and mucilages are separated as sludge by centrifugation. Kaimal, TNB et al., Indian Patent No. 183639, 2000 discloses a process for simultaneous removal of gums and waxes in a single step. The process for the preparation of purified bran oil by simultaneous dewaxing and degumming comprises stirring rice bran oil with water in the ratio of 1:0.1 to 1:1 at a temperature in the range of 48 to 70° C. for a period of at least 30 minutes, centrifuging the above mixture for a time period in the range of 4 min. to 60 min. at 7000 to 8000 rpm, optionally repeating the above said steps to obtain clear purified rice bran oil. In this procedure, a higher amount of water was used to remove the gums and waxes. This process is efficient, economical and convenient in removing both the gums and waxes in a single step. Apparently, the high surface activity of the glycolipids present in the oil is responsible for the simultaneous removal of two components in an emulsified form. It was observed that, when the process is repeated a second time, a small amount of sludge is obtained which contains considerable amount of glycolipids (Unpublished observation). This sludge forms the starting material for the isolation of glycolipids by the present invention.

Rice bran oil has an unusually high content of glycolipids (6%) constituted by a an enriched form from the sludge generated during the simultaneous degumming/dewaxing process earlier developed for rice bran oil processing. This product has an abnormally high capacity to absorb water. The analysis of dehydrated product showed that it contained 74– 80% glycolipids, 20–26% neutral lipids and 0–6% phospholipids. The neutral lipid fraction contained 60–70% monoglycerides, the glycolipid graction contained many novel glycolipids such as ceramides, glyceroglycolipids, steryl glycolipids, sphingolipids etc. and the phospholipid fraction was found to contain phosphatidyl choline as a major component. This mixture of components was isolated in the form of a white creamy aqueous emulsion that is stable for several days at 20° C. The glycolipids thus isolated have potential applications in cosmetics/pharmaceutical/food industries.

The present invention provides an improved and cost effective process for the isolation of a glycolipid enriched fraction from crude rice bran oil, which may optionally be further purified to obtain pure glycolipids, from the sludge obtained during simultaneous dewaxing and degumming of the crude oil by an earlier patented process and consists of treating the sludge obtained from the second stage of the said process to hexane extraction, centrifugation and lyophilization to yield a product containing 70–80% of glycolipids including the novel phosphoglycolipids that are uniquely present in rice bran oil.

A process for the simultaneous dewaxing and degumming of rice bran oil involving the at least two-stage treatment of the crude oil with boiling water whereby the waxes and gums are emulsified together and are separated is known.

Such a simple process work in the present case due to the unusual composition of rice bran oil and would not work with other vegetable oils. Analysis of the sludge obtained at both stage showed that they were qualitatively very different in their compositions and that the sludge obtained from the second water treatment contained predominantly glycolipids and neutral lipids. This forms the basis of the present invention. Thus, though the present invention utilizes an earlier patented process, the aim was different. The earlier process was intended to make crude rice bran oil free of waxes and gums while the present process utilizes the separated components as a raw material for the isolation of a high value product. The end products in both inventions are different though utilizing a common processing step. It would also be not obvious even to those experienced in the art that the sludge produced could be the source of glycolipids. Further, the process would be applicable only to rice bran oil and not to other vegetable oil due to differences in composition of this oil compared to other vegetables oils, the differences being the presence of usually high content of surface active lipids, high content of waxes, high contents of non-saponifiable lipids and high contents of free fatty acids.

The main objective of the present invention was, therefore, to establish a process for the isolation/recovery of glycolipids, a mixture of glyceroglycolipids, sphingolipids, ceramides etc, (either in fraction or as whole) from the sludge produced during the simultaneous degumming/dewaxing of rice bran oil as detailed in an earlier patent (Kaimal, T. N. B., et. al, Indian Patent No. 183, 639, 2000). The present invention consists of (a) a hot water treatment previously subjected to the degumming/dewaxing process of the oil, (b) washing of the sludge this formed with hexane to remove the neutral lipids present (c), drying of the sludge in the lyophilized to remove all the water absorbed, and (d) (optional) separation of different components of the dried sludge by column chromatography and receiving the glycolipids present in the sludge.

Thus, the present process utilizes a low-value byproduct from an earlier patented process to obtain a high-valve product that has potential applications in a variety of fields such as food, pharmaceuticals and cosmetics. The product is also afforded by a very simple process, much simpler than any known process for isolation of glycolipids from natural sources. The presence of novel glycodlipids in the concentrate obtained add further value to the product. They may optionally be further purified and individual components isolated from the mixture by methods known in prior art.

The following examples are given by way of illustrations and therefore, should not be construed to limit the scope of present invention.

EXAMPLE 1

Part I

Six hundred grams of crude rice bran oil (A) having phosphorus of 350 ppm, free fatty acid content of 7.19% and wax content of 3.54% was first subjected to simultaneous degumming/dewaxing. Thirty milliliters of boiling water of water above 95° C. was added to the oil under stirring and then stirred vigorously for 1 hour to get a stable emulsion. The stirring was done with the help of a mechanical stirrer. The emulsion was allowed to settle for two hours. This was centrifuged at seven thousand r.p.m. for 30 minutes. The sludge that settled at the bottom contained mainly waxes, gums, occluded oils and a small percentage of glycolipids. The supernatant oil (B) having phosphorus content of 23.2 ppm, free fatty acid content of 7.21% and wax content of 0.23% was degummed/dewaxed a second time with 10% (w/w) boiling water of water above 95° C. Five hundred grams of (B) was taken an fifty milliliters of boiling water was added to it and stirred vigorously for 45 minutes with the help of a mechanical stirrer. The emulsion formed was centrifuged again at 7000 r.p.m for 30 minutes to yield an oil (C) with 16.1 ppm of phosphorus, 7.0% of free fatty acids and 0.08% of wax.

Part II

The sludge at the bottom of the centrifuge tube was dispersed in hexane and then centrifuged again at 7000 r.p.m. for 20 minutes. The supernatant hexane layer (containing neutral oil, phospholipids etc). was decanted. The residual sludge after second time washing with hexane and followed by centrifugation, was collected and dried completely using a lyophilizer at −51° C. and under vacuum (0.2 mm of Hg). The dried product (2.15 g) was analyzed and the major portion (76%) of the isolated product was found to be a mixture of various glycolipids, the rest being neutral lipids. This product may be used in foods/medicinal/cosmetics formulations directly.

Purification Step (Optional)

The glycolipid fraction can be purified further, if desired, by column chromatography as described below 0.57 grams of the dried product were absorbed on to a silicic acid column. The neutral lipids were eluted with bexane and ethyl acetate by gradually increasing the polarity up to a 75.25 (hexane:ethyl acetate) mixture. In this procedure, 0.12 grams of neutral lipids were obtained. The glycolipids present in the dried sludge were eluted with acetone and 0.43 grams of glycolipids were obtained. Then the column was eluted with methanol to elute out the phospholipids present (if any). However, it was found that there was no phospholipid present in the sludge. It was in agreement with the fact that the reduction of phosphorus level from the oil (B) to oil (C) was almost negligible. Moreover, it was chemically found that the glycolipid isolated from the column was having phosphorus in it structure (positive to ammonium molybdate test and confirmed by 31P NMR). IUPAC method was followed for the determination of phospholipids and AOCS method was followed for the determination of the percent free fatty acids present TLC studies. Complete elution of neutral lipids were monitored by checking micro-TLC plates developing with hexane and ethyl acetate (75:25) and keeping the plates in iodine chambers. Elution of glycolipids were also monitored by developing micro-TLC plates in $CHCl_3$:$CH_3OH$:$H_2O$ (65:25:4) using α-naphthol/orcinol reagents.

EXAMPLE 2

In this experiment, another sample of crude rice bran oil (A) was taken which had much higher amount of phosphorus (680 ppm) and also higher amount of free fatty acids (17.5%). Five hundred grams of this oil was taken and twenty five milliliters (5% w/w) of boiling water or water above 95° C. was added to it and the stirred vigorously for one hour. It formed a stable emulsion. The emulsion was allowed to stand for two hours at room temperature. As described earlier the emulsified material was centrifuged at 7000 r.p.m. for 30 minutes. The supernatant oil (B) was collected for second water treatment. The oil was analyzed and found to have 65 ppm of phosphorus and 17.4% free fatty acids. The oil was further treated with 20% (w/w) boiling water as described in the previous example. The supernatant oil (C) was found to have 47 ppm of phosphorus and 17.4% of free fatty acids. The sludge settled at the bottom was taken for further investigations. The sludge was washed with hexane and centrifuged as described earlier. The sludge was then dried completely using a lyophilizer at −50° C. to −51° C. and 0.2 mm of Hg pressure 1.97 grams of dried products was loaded to a silicic acid column. The neutral lipid was first eluted with hexane and ethyl acetate by gradually increasing the neutral lipid was first eluted with hexane and ethyl by gradually increasing the polarity (up to 75:25 hexane:ethyl acetate). 0.334 grams of neutral lipids was obtained (16.95%). The glycolipid fraction was then eluted with acetone and was monitored with micro-TLC by using α-naphthol reagent. 1.458 grams of a mixture of glycolipids was obtained (74.01%). The phospholipid fraction was eluted was methanol and monitored with ammonium molybdate reagent. 0.118 grams (5.99%) of phospholipids were obtained. On further investigation, it was found that the phospholipid fraction contains only phospholipids choline (detected by Dragendroffs Reagent and compared with standard phosphatidyl choline).

EXAMPLE 3

In this experiment, another sample of crude rice bran oil (A) was taken which had phosphorus content of 455 ppm and free fatty acid content of 11.8%. The oil was found to have wax content of 3.46%. Five hundred grams of this oil was taken and twenty five milliliters (5% w/w) of boiling water or water above 95° C. was added to it and then stirred vigorously for one hour. It formed a stable emulsion. The emulsion was allowed to stand for two hours at room temperature. As described earlier the emulsified material was centrifuged at 7000 rpm for 30 minutes. The supernatant oil (B) was collected for second water treatment. The oil was analyzed and found to have 35.5 ppm of phosphorus and 11.6% of free fatty acids. The oil was further treated with 20% (w/w) boiling water as described in the previous example. The supernatant oil (C) was found to have 16.6 ppm of phosphorus and 11.6% of free fatty acids. The sludge settled at the bottom was taken for further investigations. The sludge was washed with hexane and centrifuged as described earlier. The sludge was then dried completely using a lyophilizer at −50° C. to −51° C. and 0.2 mm of Hg pressure 2.34 gms of dried products was obtained. 2 grams of the dried product was loaded to a silicic acid column. The neutral lipid was first eluted with hexane and ethyl acetate by gradually increasing the polarity (up to 75:25 hexane:ethyl acetate). 0.34 grams of neutral lipids was obtained (17%). The glycolipid fraction was then eluted with acetone and was monitored with micro-TLC by using α-naphthol reagent. 1.44 grams of a mixture of glycolipids was obtained (72%). The phospholipid fraction was eluted with methanol and monitored with ammonium molybdate reagent 0.118 grams (5.9%) of phospholipids were obtained.

Those skilled in the art will appreciate that the invention described herein is susceptible to variations and modifications other than those specifically described. It is to be understood that the invention includes all such variations and modifications.

The Major Advantages of Present Invention Are

1. The process uses a low-value byproduct for the recovery of a high value product.
2. The process is simple, cost-effective and does not involve any costly chromatographic steps as in conventional processes for isolation of glycolipids.
3. The process can easily be exploited commercially as it does not entail high capital costs.
4. The recovery of glycolipids is quite high and it is in the range of 70–80%.
5. The recovered product can be utilized in cosmetics/pharmaceuticals/food formulations.

We claim:

1. A process for the isolation of a glycolipid enriched fraction from rice bran oil, said process comprising (i) subjecting crude rice bran oil to dewaxing/degumming at least two times with formation of a sludge as a by product and, (ii) treating the sludge obtained as a byproduct to hexane extraction, and separating the glycolipid enriched fraction thereby obtaining the glycolipid enriched fraction.

2. A process as claimed in claim 1 wherein the glycolipid fraction is purified to obtain substantially pure glycolipids.

3. A process as claimed in claim 2 wherein the purification of the glycolipid fraction is done by column chromatography.

4. A process as claimed in claim 1 wherein the glycolipid fraction is separated by centrifugation and lyophilisation.

5. A process for the isolation of a glycolipid fraction from rice bran oil, said process comprising degumming/dewaxing crude rice bran oil by adding boiling water thereto with stirring to form an emulsion, separating the emulsion thus obtained into a supernatant fraction and sludge, subjecting the supernatant fraction to further degumming/dewaxing by adding water at elevated temperature with stirring, separating the resultant emulsion into a supernatant fraction containing substantially pure oil and a sludge, extracting at least once the sludge so obtained with hexane followed by separating the glycolipid fraction.

6. A process as claimed in claim 5 wherein the glycolipid fraction is purified to obtain substantially pure glycolipids.

7. A process as claimed in claim 6 wherein the purification of the glycolipid fraction is done by column chromatography.

8. A process as obtained in claim 5 wherein the glycolipid fraction is separated by centrifugation and lyophilisation.

* * * * *